United States Patent [19]

Turner

[11] Patent Number: 4,658,836
[45] Date of Patent: Apr. 21, 1987

[54] BODY PASSAGE INSERTABLE APPLICATOR APPARATUS FOR ELECTROMAGNETIC

[75] Inventor: Paul F. Turner, North Salt Lake, Utah

[73] Assignee: BSD Medical Corporation, Salt Lake City, Utah

[21] Appl. No.: 750,483

[22] Filed: Jun. 28, 1985

[51] Int. Cl.[4] .............................................. A61N 5/04
[52] U.S. Cl. ................................. 128/804; 128/736; 128/642
[58] Field of Search ................ 128/303.1, 303.12, 399, 128/736, 783, 784, 804, 642

[56] References Cited

U.S. PATENT DOCUMENTS

| | | | |
|---|---|---|---|
| 2,407,690 | 9/1946 | Southworth | 128/422 |
| 4,148,005 | 4/1979 | Larsen et al. | 128/736 |
| 4,224,949 | 9/1980 | Scott et al. | 128/642 |
| 4,253,469 | 3/1981 | Asland | 128/736 |
| 4,312,364 | 1/1982 | Convert et al. | 128/804 |
| 4,378,806 | 4/1983 | Henley-Cohn | 128/804 |

FOREIGN PATENT DOCUMENTS

| | | | |
|---|---|---|---|
| 0105677 | 4/1984 | European Pat. Off. | 128/804 |
| 1145279 | 2/1960 | Fed. Rep. of Germany | 128/804 |
| 1220945 | 8/1962 | Fed. Rep. of Germany | 128/804 |
| 2417263 | 4/1974 | Fed. Rep. of Germany | 128/804 |
| WO81/03616 | 12/1981 | PCT Int'l Appl. | 128/804 |

*Primary Examiner*—Edward M. Cohen
*Attorney, Agent, or Firm*—Hubbard, Thurman, Turner & Tucker

[57] ABSTRACT

A body passage or cavity insertable applicator apparatus for electromagnetic radiation (EMR) systems, particularly for medical hyperthermia use, comprises an elongate applicator having coaxial inner and outer conductors electrically conducted at an EMR input end to a conventional coaxial transmission line for transmitting high frequency EMR from a source to the applicator. The applicator outer conductor is longitudinally split on opposite sides to form first and second outer conductor segments, the inner conductor being electrically connected, at an applicator termination end to one of such segments. A dielectric media is disposed between the applicator inner and outer conductors, and the outer conductor and termination end are covered by a dielectric sheath. A substantially uniform, external electric tissue heating field is obtained along substantially the entire length of the applicator by exponentially increasing thickness of the dielectric sheath towards the termination end and making thickness of the sheath over the termination end equal to at least half the outer diameter of the applicator. Cooling means comprising a flexible envelope disposed around the applicator and cooling fluid flow means are provided for tissue surface cooling, the cooling fluid in the envelope also enhancing dielectric field coupling into tissue being irradiated. Several applicator variations are described, including an applicator in which the outer conductor segments are helically wrapped to enhance flexibility.

11 Claims, 16 Drawing Figures

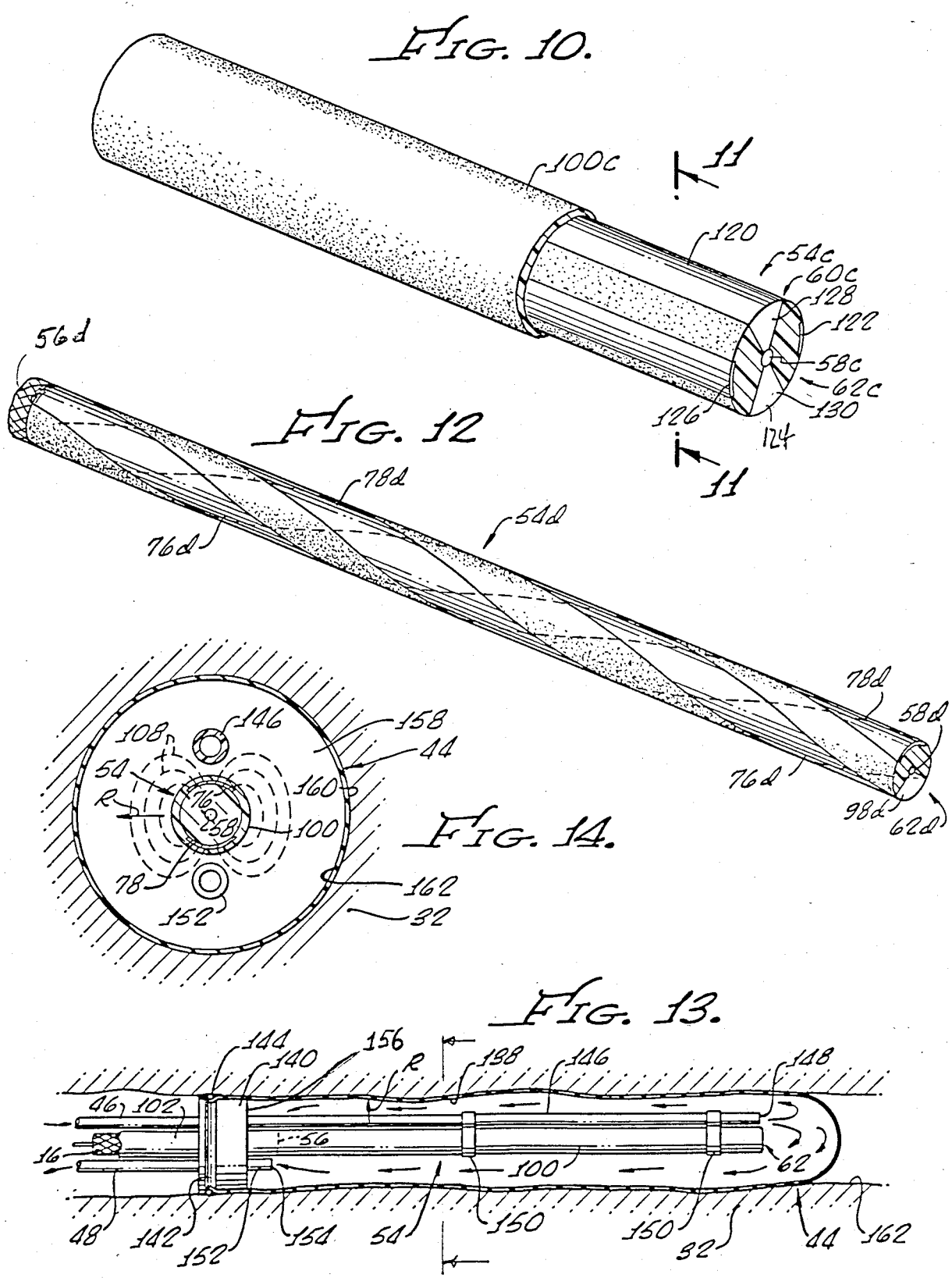

BODY PASSAGE INSERTABLE APPLICATOR APPARATUS FOR ELECTROMAGNETIC

The present invention relates generally to the field of apparatus for irradiating human and animal tissue with electromagnetic radiation for medical hyperthermia purposes, and more particularly to body insertable radiation applicators associated with such hyperthermia apparatus.

Hyperthermia or induced high body temperature has, for many years, been considered beneficial in treating various human diseases, very importantly including many types of cancer. For example, some types of malignant cells can reportedly be destroyed by heating to temperatures slightly below that injurious to most normal cells. Furthermore, some malignant cell masses having poorer heat dissipation characteristics than normal tissue, presumably due to abnormally low blood circulation, are subject to preferential hyperthermia treatment. As a result, such malignant cell masses can often be heated to temperatures substantially higher than that of surrounding healthy cells, to enable hyperthermia treatment, even when both types of cells are heated simultaneously. This characteristic not only enables hyperthermia treatment of some types of malignancies which are no more temperature sensitive than normal cells, but usually permits much shorter hyperthermia treatment times, even of thermally sensitive malignancies, as is important for various medical reasons.

More specifically, various types of malignant growths are considered by many researchers to have a relatively narrow hyperthermia treatment temperature range. Below a threshold temperature of about 41.5° C. (106.7° F.), thermal destruction of these malignancies is not believed to occur; for hyperthermia temperatures below this threshhold, growth of some of these malignancies may tend to be stimulated. In contrast, at temperatures above a range of about 43° C. to 45° C. (109.4° F. to 113° F.) thermal damage even to most normal cells occurs, the exposure duration at any elevated temperature being also a significant factor. Accordingly, if large or critical parts of human body are heated into, or above, the 43° C. to 45° C. range for even relatively short durations, serious permanent injury or death is possible.

Some types of skin cancers are known to respond to direct application of surface heat. However, deeply located malignant growths, due to normal blood flow body heat transfer properties of the body, can rarely be heated to a destructive temperature in such manner without overlying healthy tissue being excessively damaged.

As a consequence, a promising alternative technique for inducing hyperthermia is electromagnetic radiation (EMR) heating. In the late nineteenth century, alternating electric currents at frequencies above about 10 KHz were discovered to cause heating in human tissue. Such (then) high frequency currents were subsequently used for thermally treating various bodily disorders such as infected tissue and injured muscles. In the early twentieth century, the term "diathermy" was introduced to describe this tissue heating caused by conversion of high frequency electric currents into heat.

Treatment of malignant growths by high frequency EMR induced hyperthermia was described as early as 1933 by Dr. Schereschewsky, in his article "Biological Effects of Very High Frequency Electromagnetic Radiation" which appeared in *RADIOLOGY* in April of that year. Experimental EMR induced hyperthermia treatment of tumors in mice at frequencies up to 300 MHz was reported in the article and a survey of research activity in the field was given. More currently in 1974, Guy, Lehman and Stonebridge presented a historical background of high frequency EMR hyperthermia research and discussed recent experimental activity in the field in their article "Therapeutic Applications of Electromagnetic Power", (PROCEEDINGS OF THE IEEE, Volume 62, No. 1, January, 1974).

In spite of encouraging results in using EMR induced hyperthermia for treatment of malignant growths, a persistent, serious problem has been experienced with thermally destroying malignant cells without, at the same time, causing excessive amounts of thermal damage to adjacent or overlying healthy cells. Such thermal damage to healthy cells may, for example, be a result of excessive EMR power density, improperly selected EMR frequencies affecting depth of penetration, or by heat concentrations or "hot spots" of standing energy waves caused by uncontrolled EMR energy reflections at boundaries between different types of body tissue layers, such as adjacent layers of fat and muscle.

Still requiring further definition and investigation are also the potentially injurious nonthermal effects of low level electromagnetic radiation. These nonthermal effects, apparently caused by electromagnetic forces acting on cell molecules, include realignment of cell molecules into undesirable, chain-like formations, coagulation of cell molecules, other damage to normal cells which may actually lead to cancer and a myriad of other undesirable physiological effects.

As an example of these physiological side effects, low EMR levels have been observed to cause such anomalies of the central nervous and cardiovascular systems as descreased arterial pressure and reduced heart rate. The Soviets have reported these adverse side effects at EMR densities as low as 10 milliwatts per square centimeter. A more detailed discussion of these nonthermal effects is found, for example, in a fairly recent article by Johnson and Guy, entitled "Nonionizing Electromagnetic Wave Effects in Biological Materials and Systems" (*PROCEEDINGS OF THE IEEE*, Volume 60, No. 6, June 1972).

Because of these potentially harmful, and generally still not completely understood, nonthermal EMR effects on healthy body tissue, the United States has established a maximum power density for prolonged EMR exposure at 10 milliwatts per square centimeter, the Soviets having established the much lower maximum of 0.01 milliwatts per square centimeter. Since EMR hyperthermia (and diathermy) apparatus commonly radiate power densities of as high as one watt per square centimeter during treatment, considerable research into nonthermal EMR effects on healthy cells is still needed, to enable development of improved EMR hyperthermia treatment technique and investigation of nonthermal efforts.

Broad band EMR hyperthermia apparatus, particularly adapted for research, have been disclosed, for example, in my copending United States patent applications, Ser. Nos. 002,583 and 002,584, both filed on Jan. 11, 1979.

In general, however, electromagnetic radiation applicators of these and other disclosed EMR hyperthermia have been configured for irradiating living tissue, or tissue simulating matter often used in research from outside the body. EMR heating of subsurface growths from an exterior surface is ordinarily enabled by configuration and placement of one or more applicators and by appropriate selection of EMR frequency, phase and intensity.

As can be appreciated, however, many malignant growths positioned deep within a body, particularly those located inside of, or in close proximity to, heat sensitive tissue or organs, are much more effectively and safely heated by EMR irradiating applicators positioned within the body as closely as possible to the growth requiring treatment.

Advantages of positioning the EMR applicators relatively close to the growth to be heated by radiation include improved heating control, more localized heating and consequently less possibility of overheating adjacent healthy tissue and elimination of standing wave "hot spots" caused by wave reflections at tissue layer boundaries.

Such close applicator access to certain types of malignant growths may be possible by surgical procedures in which overlaying layers of tissue are cut. When surgical access techniques are practical, small EMR applicators, usually of the same type used for surface radiation, are placed over or in the incision to provide more direct irradiation of the growth.

However, for many common occurring, deeply located tumors, surgical access for the applicator may be impossible or impractical for many reasons, including the reason that a patient may be unable to withstand the rigors of a major operation.

For those relatively common malignancies which are located close to or along a naturally occuring body passage, such as cancer of the esophagus, larynx, prostrate gland and colon, applicator access is readily provided by the passages, through the associated bodily orifice. An illustrative type of a corresponding body passage insertable EMR applicator is described in the U.S. Pat. No. 2,407,690 of Southworth.

However, special and difficult problems associated with radiation heating of many prevalent types of malignancies found along body passages are caused by tendency of the growths to spread around and along the passage, often in a relatively thin layer. Typically, the malignant layer may be less than a centimeter thick and may extend as far as 6-10 centimeters along the passage.

Relatively uniform irradiation heating of the entire malignancy is necessary to prevent excessively high energy levels possibly causing thermal damage to surrounding healthy tissue, from being applied to some malignant regions, while low irradiation levels, possibly causing only growth stimulating temperatures, are applied to other malignant regions. Thus, the applied EMR field should provide an elongated heating pattern which is generally cylindrically uniform in configuration.

Heretofore, however, body passage insertable EMR applicators, such as the type disclosed in the Southworth patent, have been configured in a manner causing a heating pattern that tends to be concentrated at the radiating tip of the applicator and which decreases at a usually exponential rate from such tip towards the radiation source.

Applicant has, however, invented a body passage or cavity insertable EMR applicator principally adapted for medical hyperthermia purposes, which provides the generally cylindrical or longitudinally uniform EMR heating pattern necessary to enable substantially uniform heating of malignant growths or other tissue diseases associated with body passages or cavities.

To achieve such longitudinally uniform, electric tissue heating field, applicant's body insertable, electromagnetic radiation applicator apparatus for irradiating living tissue and the like, comprises an elongate, generally cylindrical applicator adapted for inserting into a body passage or cavity through a natural body orifice or an incision. The applicator, which has a length substantially greater than an outer diameter thereof, is formed of concentric inner and outer conductors separated by a dielectric media, the outer conductor being longitudinally split to form generally symmetrical, spaced apart first and second, arcuate outer conductor segments.

Included in the applicator apparatus, is an electrical conductor which interconnects, at a termination end of the applicator, the inner conductor with one of the first and second outer conductor segments. Electromagnetic radiation transmission means, for example, a coaxial cable, are connected to the applicator inner and outer conductors at radiation receiving ends thereof, for transmitting electromagnetic radiation energy thereto from an electromagnetic radiation source. Means are also included for causing an external electric tissue heating field radiated by said applicator to be substantially uniform at substantially all transverse cross sections along an applicator to thereby provide substantially uniform tissue heating along the applicator.

More specifically, to force the electric field outside the applicator for radiation heating of surrounding tissue, spacings between adjacent pairs of outer conductor segment edges preferably having defining angles of 90°, thereby also causing both outer conductor segments to be quarters of a cylindrical surface.

The means for causing the external, electric tissue heating field to be uniform along the length of the applicator preferably comprises a dielectric sheath covering the outside of the applicator which increases in radial thickness at a selected exponential rate towards an applicator termination end. Covering the termination end, thickness of the dielectric sheath is at least about one half as great as the outer diameter of the applicator.

Increasing radial thickness of the dielectric sheath in this manner increases sheath impedance towards the applicator termination end. This increased dielectric sheath impedance in turn reduces the radiated electric tissue heating field towards the termination end at a rate off setting or compensating for the characteristic increase of external electric field towards the termination end associated with the applicator configuration. As a direct result, the electric tissue heating field radiated by the applicator is longitudinally uniform to enable longitudinally uniform tissue heating. Although, it is to be appreciated that malignant growth regions in the body passage along the inserted applicator may be heated to higher temperatures than normal tissue elsewhere along the applicator, due to poorer heat dissipation properties of the malignant growths.

Dielectric sheath thickness increase towards the termination end may be accomplished with either of two configurations. In a first configuration, sheath thickness is increased while maintaining constant outer conductor diameter, thereby causing the applicator apparatus outer diameter to increase towards the termination end. Where this may be undesirable, for example, for insertion reasons, the outer conductor diameter may be decreased consistant with radial sheath thickness increase to maintain a constant applicator apparatus diameter.

In one variation, edge spacing between the outer conductor segments decreases towards the applicator termination at a rate causing the radiated electric field to be constant along the applicator, the dielectric sheath being formed having uniform radial thickness.

In another applicator variation, which employs the same means for providing the longitudinally uniform electric field, the outer conductor segments may be formed in a helical configuration to enhance applicator flexibility, as may be desired for some uses.

Still another applicator variation has the outer conductor thereof split into four, rather than two, equally spaced apart conductor segments. With such configuration, the external electric tissue heating field provided may be slightly more circumferentially uniform, as may be desirable where existing tissue "thermal smearing" properties, caused by flood flow, are poor.

Cooling means may be provided with any of the applicators to enable surface cooling of body tissue when the applicator is inserted in a body passage or cavity for deep irradiation heating thereof. Included in the cooling means is a flexible, tissue shape conforming bladder which is disposed, in fluid sealing relationship, around the applicator. Fluid inlet and outlet lines communicate from an inside to an outside of the bladder to enable flow of cooling fluid from a source therethrough.

To enhance electric field coupling into tissue being irradiated by the applicator apparatus, the cooling fluid comprises a dielectric media (such as distilled water) having a dielectric constant substantially equal to that of the tissue. The cooling fluid dielectric in the bladder between the applicator and the surrounding tissue eliminates electric field anomalies which would otherwise be caused by air voids in such regions.

A better understanding of the present invention may be had from a consideration of the following detailed description, taken in conjunction with the accompanying drawings, in which.

Figure 6A:
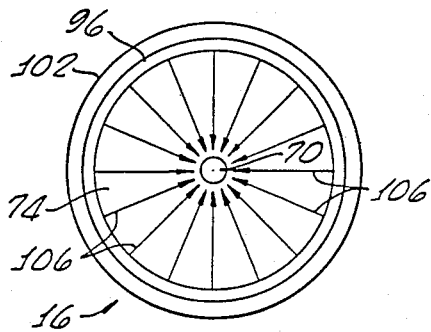
Figure 6B:
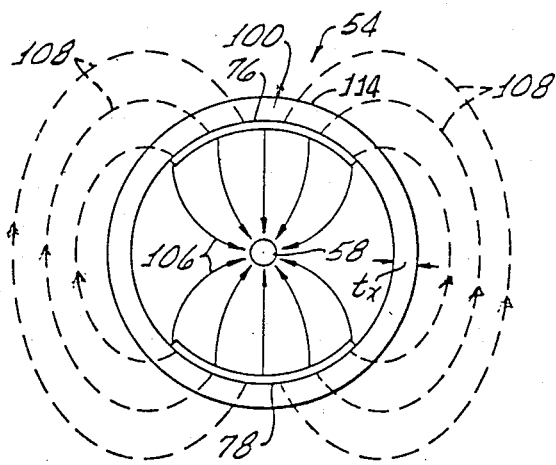
Figure 6C:
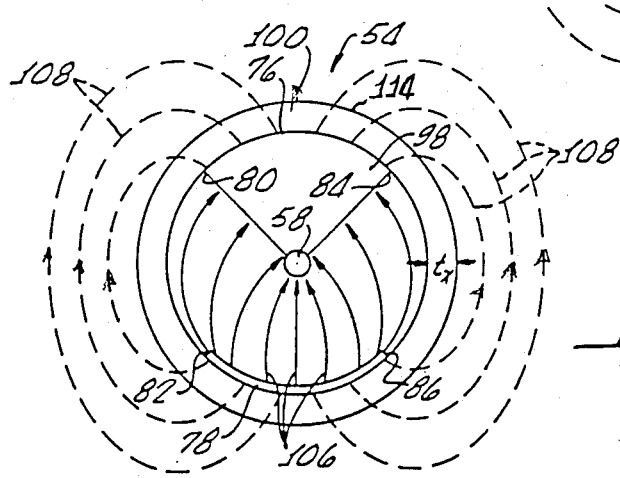
Figure 7:
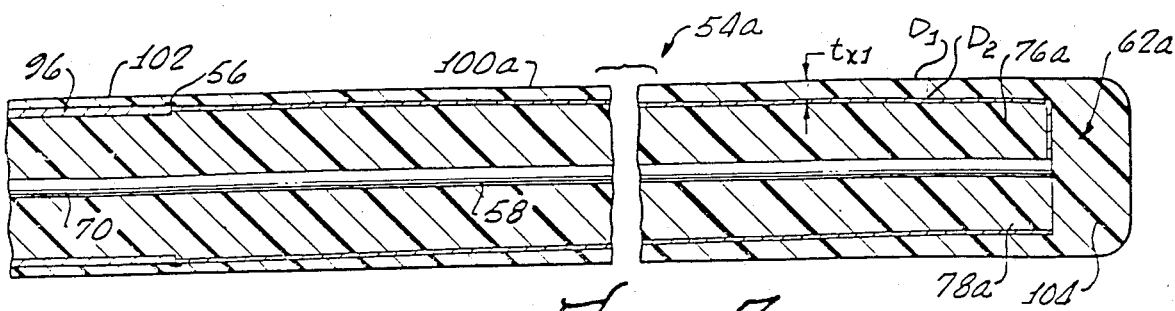
Figure 8:
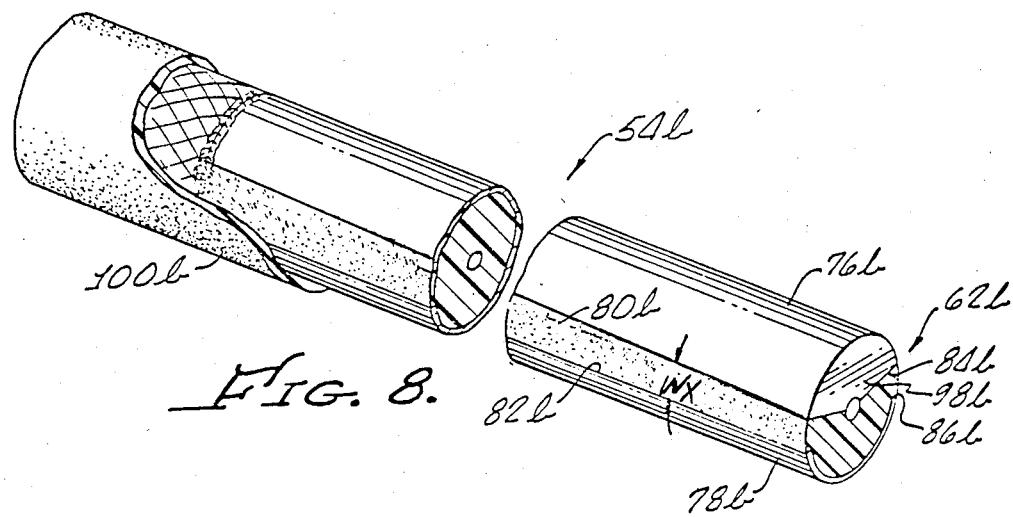
Figure 9:
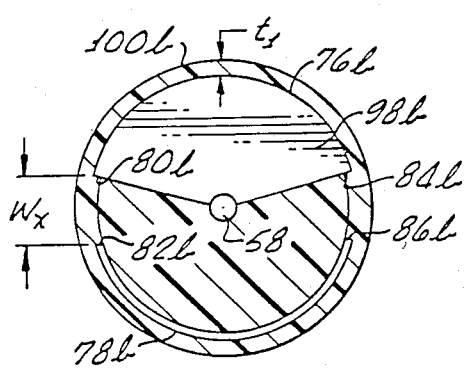
Figure 11:
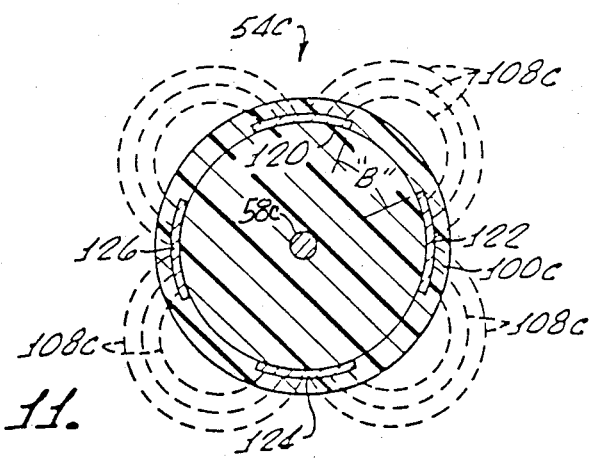

FIG. 6 is a pictorial diagram depicting general configuration of transverse electric tissue heating fields radiated by the applicator, FIG. 6(a) depicting the transverse electric field associated with a transverse cross section of the applicator relatively adjacent to the termination end thereof; FIG. 6(b) depicting the transverse electric field associated with the transverse cross section of the applicator relatively adjacent the center thereof and FIG. 6(c) depicting the transverse electric field associated with the transverse cross section through a coaxial EMR transmitting cable connected to the applicator and adjacent to such connection;

FIG. 7 is a partially cutaway perspective drawing of a first applicator variation in which outside diameter thereof is maintained constant, while dielectric sheath thickness increases towards the emitting end to attain a longitudinally uniform, radiated electric heating field;

FIG. 8 is a partially cutaway perspective drawing of a second applicator variation in which the longitudinally uniform, radiated electric heating field is attained by reducing edge spacing between first and second outer conductor segments towards a termination end while maintaining constant radial thickness of a dielectric sheath covering the applicator;

FIG. 9 is a termination end view of the second applicator variation of FIG. 10, showing closer edge spacing between first and second outer conductor segments at the termination end;

FIG. 10 is a partially cutaway perspective drawing of a third applicator variation in which the outer conductor is longitudinally split into first, second, third and fourth conductor segments in a symmetrical manner;

FIG. 11 is a transverse cross sectional view, taken along line 11—11 of FIG. 10 showing mutual circumferential spacing of the four outer conductor segments of the third application variation, and also showing a typical transverse electric heating field pattern radiated thereby.

FIG. 12 is a partially cutaway, perspective drawing of a fourth applicator variation in which the first and second outer conductor segments are configured in helical form to enhance applicator flexibility;

FIG. 13 is a partially cutaway perspective drawing of a fifth applicator variation having tissue surface cooling means; and FIG. 14 is a transverse cross section view, taken along line 14—14 of FIG. 13, showing a cooling means disc fixed to the applicator at an EMR input end of the applicator and having cooling fluid inlet and outlet tubes mounted therethrough.

Figure 1:
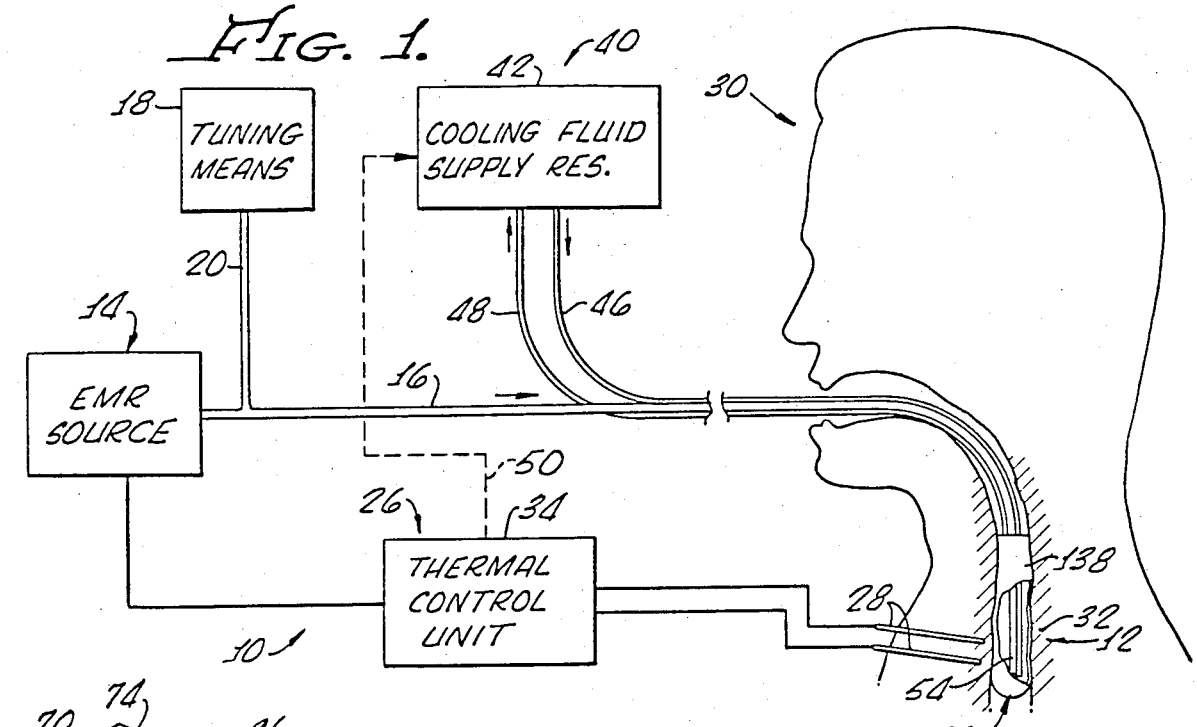
FIG. 1 is a schematic diagram, showing in partial block diagram and in partial cutaway form, an electromagnetic radiation (EMR) system which incorporates a body passage or cavity insertable EMR applicator in accordance with the present invention.

Shown in FIG. 1, in generally block diagram form, in an exemplary electromagnetic radiation (EMR) hyperthermia system 10, which incorporates a body passage or cavity insertable applicator apparatus 12, in accordance with the present invention. The system 10 is particularly configured and adapted for heating, by electromagnetic radiation in the radio frequency or microwave frequency spectrum, of body tissue for medical hypothermia treatment of thermally controllable diseases, including many types of malignant growths. In a research environment, the system 10, including the applicator apparatus 12, may be used to heat, by high frequency EMR, animal body tissue or tissue simulating matter.

Included as part of the system 10 are a conventional EMR source 14 connected to the applicator apparatus 12 by a transmission line 16, which may comprise a conventional coaxial cable. Conventional transmission line tuning means 18, for protecting the source 14 from reflected EMR waves and for improving system efficiency, may be connected to the line 16 by an additional transmission line 20. In the exemplary system 10, the EMR source 14 is shown controlled by conventional thermal control means 26 which preferably includes a plurality of thermal probes or thermocouples 28. Such thermocouples 28 are adapted for monitoring tissue temperature when inserted into a body 30, in a body passage or cavity region 32 thereof, which is to be EMR heated by the applicator apparatus 12. Connected between the source 14 and the thermocouples 28 is a conventional thermal control unit 34 programmable to control operation of the EMR source in a manner providing a preselected time/temperature tissue heating profile, as monitored by the thermocouples.

Operatively associated with the applicator apparatus 12, and thus also forming part of the system 10, are tissue surface cooling means 40. Included in the cooling means is a conventional cooling fluid supply and reservoir 42 which is connected to a flexible fluid cooling portion 44 of the applicator apparatus 12 by fluid supply and return lines 46 and 48, respectively. The cooling means 40 and the applicator cooling portion 44 cooperate, as described below, to cool surface and near-surface layers of the body region 32 being irradiation heated by the applicator apparatus 12, thereby enabling deep heating without excessive surface tissue heating. As indicated by the broken line 50, operation of the cooling supply and reservoir unit may be controlled by the thermal control unit 34 in a conventional manner.

Also as described below, cooling fluid pumped by the fluid supply and reservoir 42 through the applicator cooling portion 44 additionally functions as a void-filling dielectric to improve electric field coupling between the applicator apparatus 12 and the tissue region 32 being heated. This dielectric function is particularly important when surfaces of the tissue passage region 32 are irregular, as is often the case when malignant growths are present, or when the passage is larger than the applicator.

Other than as specifically described below, most portions of the system 10 form no part of the present invention, which is principally directed to the applicator apparatus 12 (and variations thereof) and the cooling means 40. However, general aspects of the entire system 10 are shown and described to illustrate a manner in which the applicator apparatus 12 can be used to advantage and to provide a background for facilitating description and understanding of the apparatus.

More particularly, and as better seen in FIGS. 2 through 5, the applicator apparatus 12, (shown in these Figures with the cooling portion 44 and associated cooling means 40 omitted for clarity) comprises a generally cylindrical, elongated applicator 54, having a length substantially greater than an outside diameter thereof. An EMR input or receiving end 56 of the applicator 54 is electrically connected to the coaxial transmission line 16. The applicator 54 includes (concentric) inner and outer conductors or radiating elements 58 and 60, respectively, which extend an entire length "1" of the applicator, from the upstream end 56 to a termination end 62. Preferably the inner conductor 58 is formed as a continuation or extension of a corresponding inner conductor 70 of the coaxial transmission line 16.

Filling the region between the inner and outer conductors 58 and 60 is a dielectric media 72 which is preferrably a continuation of a corresponding dielectric media 74 of the transmission line 16. The dielectric media 72 may, for example, be teflon and have a dielectric constant, e, of approximately 2.5 for the apparatus operating frequency mentioned below.

To attain the desired radiated electric field characteristics, opposite sides of the outer conductor 60 are longitudinally split along the entire applicator length "1" (FIG. 3), in a manner dividing the outer conductor into longitudinally symmetrical, arcuate first and second outer conductor (radiating elements) segments 76 and 78, respectively, both adjacent pairs of outer conductor segment edges 80, 82 and 84, 86 being thereby, spaced apart a uniform distance "w" for forcing an electric heating field outside of the applicator 54, the opposite angles "A" (FIG. 4) which define the edge spacings between the outer conductor segments 76 and 78 are preferably equal to about 90°, the two outer conductor segments 76 and 78 thereby each defining longitudinal quarters of a cylindrical surface.

At the applicator input end 56 (FIG. 3), ends of the outer conductor segments 76 and 78 are electrically connected, as by soldering, to a corresponding outer conductor 96 of the coaxial transmission line 16, to provide an electrical extension thereof. Assuming the line 16 comprises a conventional coaxial cable, the outer conductor 96 thereof is of braided wire configuration; in contrast, the outer conductor segments 76 and 78 of the applicator 54 are each formed of a single sheet of a conductive material such as copper.

To enable the desired outwardly radiated electric heating field along the applicator 54 (FIGS. 2 & 3), the applicator inner conductor 58 is connected, at the termination end 62, to either one of the outer conductor segments 76 or 78 by a quarter circular conductive plate 98. Such connection between the inner conductor 58 and the first outer conductor segment 76 is illustrated.

Covering the entire outer surface of the applicator 54, to form an outer layer thereof, is a dielectric sheath or covering 100 which, at the EMR input end 56 of the applicator joins a corresponding outer dielectric sheath 102 of the transmission line 16, Preferrably the dielectric constant, e, of the two sheaths 100 and 102 are the same, and may, for example, be equal to approximately 2.5.

When operatively connected by the transmission line 16 to the EMR source 14 (FIG. 1) and when configured in the above described manner the applicator 54 outwardly radiates an electric tissue heating field along the length "1", as well as outwardly from the termination end 62. In this regard, it should be noted that although both electric and magnetic field are radiated from the applicator, as is inferred from the term "electromagnetic radiation", tissue heating is principally caused by the electric field, since the body is substantially "transparent" to magnetic fields. Hence, only the external electric field characteristics are considered herein. Assuming a sufficient length, 1, of the applicator 54 and proper positioning of the applicator in a diseased body passage or cavity, all portions of a malignant growth extending around and along the passage or cavity can thus be simultaneously irradiated for heating, as is normally required.

However, because of the end connection, by the plate 98, between the inner conductor 58 and the conductor segment 76, which is required to cause an external electric field along the applicator 54, the radiated electric heating field is stronger at the termination end 62 than elsewhere along the applicator length "1". Measurements during operation indicate that the radiated electric field decreases at an exponential rate away from the termination end 62 towards the EMR input end 56. That is, the external electric field increases exponentially as the termination end 62 is approached from the input end 56.

As a result, without suitable compensation, even assuming natural tissue cooling by blood flow which tends to cause relatively uniform tissue heating or "thermal smearing", the exponentially emitted electric field which varies along the applicator 54 would result in greater tissue heating towards the termination end 62. As previously mentioned, this is undesirable, since healthy tissue near the applicator termination end 62 may be overheated and thermally damaged, while malignant cells in regions remote from the applicator termination end may be heated only to growth stimulating temperatures.

Accordingly, means are provided for causing the tissue heating electric fields to be substantially uniform at all transverse cross sections along substantially the entire applicator length "1". Although, as described below, the external electric field is not completely uniform around the applicator 54, uniform tissue heating is generally provided by the thermal smearing properties of the tissue. This thermal smearing, when insufficient, may be augmented by periodic, partial axial rotation of the applicator, or by other means described below.

Figure 2:
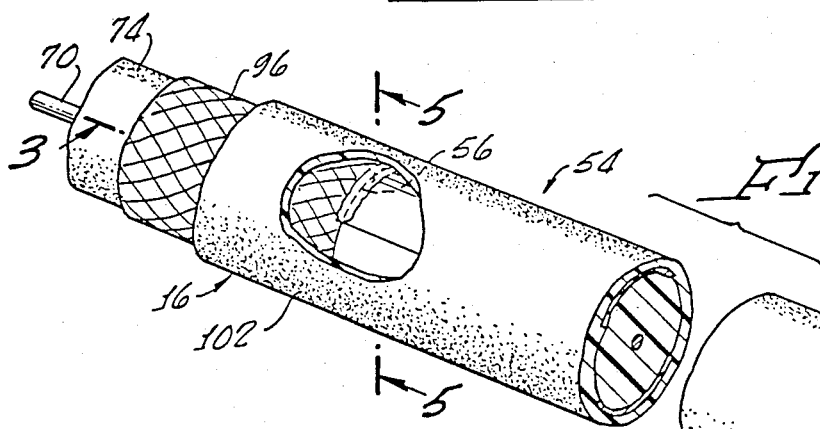
FIG. 2 is a partially cutaway perspective drawing of the EMR applicator of FIG. 1, showing longitudinal splitting of an outer conductor of a coaxial pair of conductors into first and second outer conductor segments and connecting between the center conductor and one of such segments at a termination end.
Figure 3:
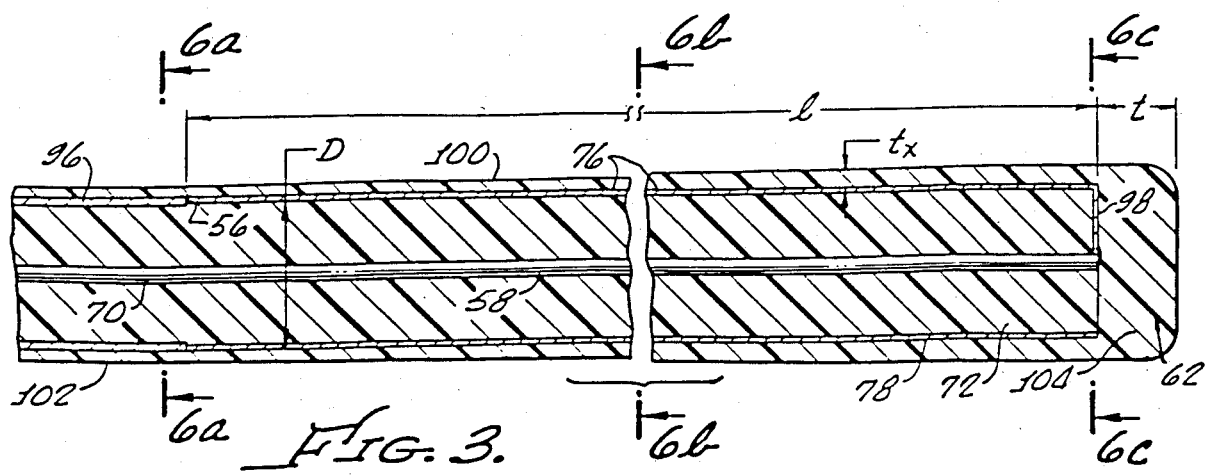
FIG. 3 is a longitudinal cross section view, taken along line 3—3 of FIG. 2, showing internal features of the EMR applicator.
Figure 4:
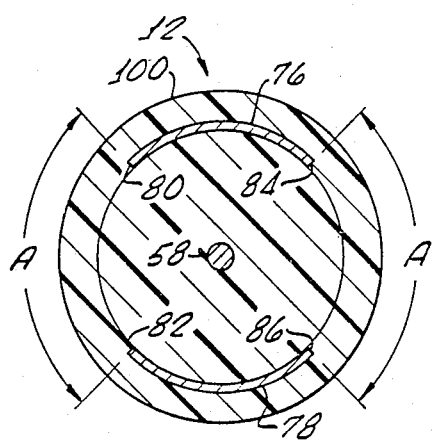
FIG. 4 is a cross sectional view, taken along line 4—4 of FIG. 2, showing a transverse section of the EMR applicator at a termination end thereof.
Figure 5:
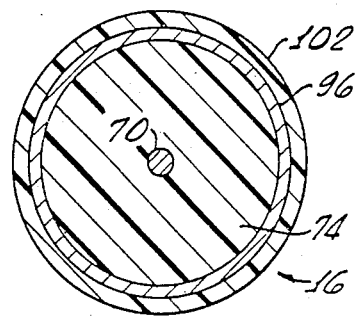
FIG. 5 is a cross sectional view, taken along line 5—5 of FIG. 2, showing a transverse section of a coaxial EMR transmission line connected to an EMR input end of the applicator.

Thermal monitoring of tissue irradiation by the applicator 54 has established that electric field uniformity along the applicator length "1" can be achieved by appropriately varying the thickness of the dielectric sheath 100 (FIGS. 2 & 3).

External radiation from the applicator termination end 62, which contributes to greater tissue heating at such end, is substantially reduced by making a thickness "t" (FIG. 3) of a transverse sheath portion 104 covering the termination end equal to at least one half an outer diameter "D" of the outer conductor 60 (FIG. 3).

Substantially uniform tissue heating along substantially the entire applicator length "1" is further attained by increasing a radial thickness "$t_x$" of the sheath 100, covering the outer conductor segments 76 and 78, at a selected exponential or increasing rate from the input end 56 towards the termination end 62. Since the intensity of the external electric field radiated by the conductors segments 76 and 78 is determined by impedance of the dielectric sheath 100, and hence depends upon sheath thickness "$t_x$", increasing thickness of the sheath towards the termination end 62 results in reduced external electric field, as is required to reduce the tissue heating at such end.

Stated otherwise, increasing the dielectric sheath thickness, "$t_x$", towards the termination end at the same exponential rate the external electric field would otherwise increase towards the termination end, eliminates what may be considered "excess" external electric field all along the applicator 54, thereby resulting in a longitudinally uniform external electric field. It is to be appreciated that there may still be some external electric field nonuniformities at the applicator ends, but because of tissue "thermal smearing" characteristics, actual tissue heating is substantially unaffected by these field nonuniformities.

Typical electric field patterns for the applicator 54 (FIG. 2) and adjacent regions of the transmission line 16 are depicted in FIG. 6(a) through (c) taken along lines 6a, 6b and 6c of FIG. 3. Internal non-tissue heating electric field lines are identified by reference numbers 106 while external, tissue heating electric field lines are identified by reference numbers 108. This external, tissue heating electric field is caused by reflection, at the applicator termination end 62, of EMR energy propogated down the transmission line 16 and applicator 54 from the EMR source 14. There is only a small external leakage field along a conventional coaxial transmission line.

As seen in FIG. 6(a), internal electric field lines 106 associated with the transmitted or forward EMR waves in the transmission line (coaxial cable) 16, assuming excitation of the fundamental or lowest order, TEM mode, are directed inwardly from the outer conductor 96 to the inner conductor 70. These field lines are typical of coaxial transmission lines, as can be seen in any microwave text.

However, at the applicator termination end 62 (FIG. 6c), the internal electric field lines 106 associated with the transmitted wave, radiate from the second outer conductor segment 78 towards both the inner conductor 58 and the connecting plate 98. The external electric field lines 108, associated with the reflected electric field, extend outwardly around the applicator 54, from the second outer conductor segment 78, to the first outer conductor segment 76. As before mentioned, the dielectric sheath 100 functions as an impedance element limiting the external electric field beyond the sheath.

In intermediate applicator regions, depicted in FIG. 6(b) the forward wave electric field lines 106 extend inwardly from the outer conductor segments 76 and 78 to the inner conductor 58. The external electric field lines 108 extend around the applicator 54 from the second outer conductor segment 78 to the first outer conductor segment 76. Because of reduced dielectric sheath thickness tx in intermediate applicator regions, compared to thickness at the termination end 62, the electric field lines 108 externally of the sheath 100 are substantially identical to those at the termination end.

From FIGS. 6(b) and (c), it is seen that strength, and hence tissue heating characteristics, of the external electric field, represented generally by spacing and concentration of the field lines 108, is greater adjacent an outer surface 114 of the sheath 100 at opposing regions of the outer conductor segments 76 and 78, along a center line through such segments and the inner conductor 70. Consequently slightly greater tissue heating may be expected in these two opposing regions. However, as mentioned above, thermal smearing characteristics are ordinarily sufficient to cause actual tissue heating to be uniform all around the applicator 54. If necessary, the applicator apparatus 12 (FIG. 1) can, however, be periodically rotated to provide added heating uniformity.

The required variation in dielectric sheath thickness, $t_x$, for any particular configuration of the applicator 54, is readily determined either by use of a conventional field strength measuring apparatus or by monitoring tissue temperature during irradiation. An appropriate variation in thickness, $t_x$, can be achieved, for example, by applying successively shorter layers of shrink-type plastic tubing over the applicator 54, more layers being applied towards the termination end 62. When the correct sheath thickness variation has been determined in this manner for the particular applicator configuration being used, production applicators are preferably constructed (as shown) having a continuously varying sheath thickness, $t_x$, as is preferable for sanitary and other reasons.

As an illustrative example, with no limitation intended or implied, the applicator 54 (FIG. 3) may be formed having a length "1" of 4 inches so that the applicator is sufficiently long to span most malignant growths expected to be found along natural body passages with which the apparatus 12 may be used. For ease of insertion through either corresponding natural body orifices or other surgical incisions, and to be compatible with typical body passage or cavity size, the outer diameter of the applicator 54, including the sheath 100 at the EMR input end 56 is 0.20 inches. Thus, the applicator 54 is compatible with standard sized coaxial cables. For use at an applied EMR frequency of 433 MHz, sheath thickness $t_x$ increases exponentially so that at the termination end 62, applicator thickness (including the sheath 100) is 0.25 inches.

When the outer diameter, length and operating frequencies of the applicator 54 are varied, external electric field characteristics may also vary and accommodations may therefore be required. For example, for higher operating frequencies, for the described applicator dimensions, the tissue heating electric field pattern tends to shift towards the termination end 62, whereas, for lower operating frequencies, the heating pattern tends to shift towards the input end 56.

By way of explanation, at higher frequencies, for example, at the standard United States diathermy frequency of 915 MHz, the conductance of body tissue increases from 1.4 mhos/meter (at 433 MHz) to 1.6 mhos/meter, due to greater tissue conductance. Thus, typical body tissue has greater thermal conductivity at higher frequencies and tends to dissipate heat faster. At the same time, capacitive impedance, $Z_c$, of the dielectric sheath 100 is inversely proportional to frequency. Since capacitive inductive decreases with increased frequency at a faster rate than body conductance increases, the net result is that tissue heating shifts toward the termination end. The reverse is true for lower operating frequencies.

Accordingly, for the same applicator configuration at higher applied frequencies, thickness $t_x$ of the dielectric sheath 100 must ordinarily be increased over that described towards the termination end 62 to maintain a uniform external electric heating field along the entire applicator length. For lower frequencies, dielectric sheath thickness, $t_x$, must ordinarily be decreased over that described towards the termination end 62.

To achieve and maintain substantially uniform tissue heating along substantially the entire applicator length "1", relationships exist between applicator length "1", outer conductor diameter "D" and the EMR operating frequency. Given substantially uniform tissue heating, as described above, when the application 54 is 4 inches long and 0.20 inches in diameter at the input end 56 and is operated at 433 MHz, similar uniform tissue heating can be expected from a corresponding applicator only half as long (2 inches) if the operating frequency is doubled to 866 MHz. If, however, for the operating frequency of 433 MHz it is desired, for example, to increase the applicator length "1" by 50% (from 4 inches to 6 inches) the outer diameter should also be increased by 50% (from 0.20 inches to 0.30 inches).

Because of possible difficulty of insertion, constructing the applicator 54 with the dielectric sheath 100 increasing in thickness, causing the applicator to be greater in diameter at the termination end 62, may, for some uses, be disadvantageous. Alternatively, the above described effect of reducing, toward the termination end 62, the external electric field strength radiated into surrounding tissue can be attained when still maintaining a constant, applicator outer diameter in variations, described below.

In the following description of several applicator variations elements and features corresponding to those previously described are given the original reference numbers followed by a subscript letter a, b, c, etc. as appropriate for the variation being described. New elements and features are given new reference numbers.

In a first applicator variation 54a (FIG. 7), a constant applicator apparatus outer diameter "$D_1$" is maintained, while still exponentially increasing thickness "$t_{x1}$" of a dielectric sheath 100a, by decreasing an outer diameter "$D_2$" of outer conductor segments 76a and 78a, (corresponding to an inner diameter of the dielectric sheath) at an exponential rate toward a termination end 62a. In this manner, the sheath thickness $t_{x1}$ exponentially increases in the necessary manner towards the end 62a without requiring applicator apparatus outer diameter to increase.

A third manner of achieving uniform tissue heating along the entire applicator length, while maintaining a constant applicator outside diameter is illustrated in FIGS. 8 and 9 for a second applicator variation 54b. In such variation 54b, a width, "$w_x$" of spacing between corresponding pairs of outer conductor segment edges 80b, 82b and 84b, 86b is decreased toward a termination end 62b while maintaining, along the length of the applicator, uniform (instead of increasing) thickness of a dielectric sheath 100b.

The edge spacing, "$w_x$" between the outer conductor segments 76b and 78b determines the extent to which the external electric field is forced outwardly from the applicator variation 54b, for example, into surrounding tissue being radiation heated. Since, as described above, with uniform edge spacing, the external tissue heating electric field increases exponentially toward the applicator termination end, the edge spacing "$w_x$" in the applicator variation 54b (FIG. 8) is decreased towards the termination end 62b at just that rate causing the external electric field to be substantially uniform along substantially the entrie length of the applicator, assuming uniform radial thickness of the dielectric sheath 100b.

Although the edge spacing, "$w_x$", is required to decrease in a manner causing capacitance of the dielectric sheath 100b between the outer conductor 76b and 78b to increase exponentially towards the termination end 62b, as is necessary to offset the otherwise exponential field increase toward the terminal end, the rate of edge spacing decrease is most easily determined by varying the spacing until either a uniform electric field along the applicator variation 54b, or a uniform heating of a tissue specimen, is attained.

Two additional applicator variations are illustrated in FIGS. 10 through 12. A third applicator variation 54c of FIGS. 10 and 11 is identical to the above described applicator 54 except that an outer applicator conductor 60c is longitudinally split into first, second, third and fourth outer conductor segments 120, 122, 124 and 126 (FIG. 11) respectively, instead of into just two outer conductor segments. The outer conductor segments 120 through 126 are preferably identical in configuration and are equally spaced apart by gap angles "B" (FIG. 11) of 45°. Two generally triangular conductive plates 128 and 130 (FIG. 10) are used to connect an inner conductor 58c to the oppositely positioned outer conductor segments 120 and 124 at the termination end 62c.

An advantage of the applicator variation 54c is that the external heating field is somewhat more nearly uniform around the applicator circumference, as can be seen by comparing the external electric field lines 108c of FIG. 11 with the lines 108 of FIG. 6(b). Accordingly, circumferential heating of some types of body tissue or malignant growths having relatively poor thermal smearing properties may be slightly more uniform, as a result periodic partial rotation of the applicator for uniform heating of such tissue or growths may be unnecessary.

A disadvantage of the applicator variation 54c is that, because of reduced spacing between edges of the outer conductor segments 120 through 126, depth of the external electric heating field is generally less, for a given power level, than for the singly split applicator 54.

Longitudinal external electric field uniformity for the applicator variation 54c is achieved in any of the above described several manners associated with the applicator 54 and the variations 54a and 54b thereof.

Flexibility of the above described applicator 54 (as well as the variations thereof) can be enhanced, as may sometimes be desirable, by helically wrapping or twisting the outer conductor segments around the applicator. Formed in this manner, a forth applicator variation 54d (FIG. 12), which is otherwise identical to the applicator 54, has first and second outer conductor segments 76d and 78d which are helically wrapped along the applicator from an input end 56d to a termination end 62d. A twisting of 1½ turns may, for example, be provided over the length of the applicator variation 54d. At the termination end 62d, an inner conductor 70d is connected to the outer conductor segment 76d by a conductive plate 98d.

In addition to improving applicator flexibility, circumferential tissue heating uniformity may be somewhat enhanced since the tissue heating electric field, as seen in the transverse section of FIG. 6(b), is rotated along the applicator variation 56d with the twisting of the outer conductor segments 76d and 78d.

Although the above described applicator 54 and variations thereof are especially adapted for EMR heating of body tissue surrounding body passages and cavities, means may sometimes be required for cooling surface layers of tissue when increased EMR power is necessary for deep tissue heating. Furthermore, when the body passage or cavity in which the applicator 54 (or any variation thereof) is inserted for tissue radiation is larger than the applicator or is irregular in shape, as may be the case when the passage or cavity walls are distorted by a maglignant growth, enhanced field coupling from the applicator into the surrounding tissue may be very desirable.

As shown in FIGS. 1, 13 and 14 for the exemplary applicator apparatus 12, the cooling portion 44, which is part of the cooling means 40, importantly provides tissue surface cooling, enabling deeper tissue heating, without excessive surface heating and at the same time enhances electric field coupling between the applicator 54 and the surrounding body tissue region 32.

Although shown used in conjunction with the first described applicator 54, it is to be appreciated that the cooling means 40 may be used with any of the several applicator variations 54(a) through 54(d) described, as well as with other application variations which may be apparent to those skilled in the art and which are accordingly within the scope of the present invention.

As shown in FIGS. 13 and 14, the applicator cooling portion 44 includes a thin, inflatable, flexible or elastormeric envelope or bladder 138 (FIG. 13) disposed around the applicator 54. To enable detachable mounting of rearward portions of the envelope 138 to the applicator 54, a plastic disc 140 is fixed to the transmission line 16 adjacent the applicator EMR input end 56.

Fluid sealing of the envelope 138 to the disc 140 is enabled by an annular groove 142 formed around the disc. An elastic band 144, or other similar retainer, is positioned around the envelope 138 in the region of the groove 142, thereby forcing rearward regions of the envelope into the groove for retaining and sealing.

Extending forwardly through the disc 140, parallel to the applicator 54, is a cooling fluid inlet tube 146, which preferably forms an extension of the fluid supply line 46. The tube 146 has a fluid discharge end 148 located relatively adjacent to the applicator termination end 62. One or more retaining bands 150 attach the inlet tube 146 to the applicator 54.

An outlet tube 152 having a return flow inlet end 154 forwardly adjacent a forward face 156 of the disc 140, extends through the disc and preferable comprises a forward end of the fluid return line 48. Conventional sealing means (not shown) are used to prevent fluid leakage around the tubes 146 and 152, at the disc 140, and between the disc and the applicator 54.

In operation, a cooling fluid 158 is pumped, at a selected cooling rate, for example, determined by the thermal control unit 24 (FIG. 1), by the fluid supply and reservoir unit 42, through the supply line 46 and inlet tube 146 into the envelope 138 (FIG. 13). Return flow of the fluid from the envelope 138 to the fluid supply and reservoir unit 42 is through the return tube 152 and return line 48.

Fluid pressure in the envelope 138 is adjusted or controlled, also, for example, by the thermal control unit 24, to expand an envelope outer surface 160 (FIG. 14) into contact with an inner surface 162 of the tissue region 32 to be EMR heated by the applicator apparatus 12. For this purpose, the envelope 138 is constructed to be sufficiently elastic and/or flexible to provide intimate envelope-tissue contact and eliminate any airpockets therebetween. This envelope-tissue contact enables the cooling fluid 158 to be circulated through the envelope 138 (FIG. 13) by the supply unit 42 in close, heat transfer relationship with the tissue region surface 162 (FIG. 14), the cooling being effective to a depth of about one of two centimeters.

Whereas the uncooled applicator 54 may be limited to safe operating levels of 10–20 watts, the cooling means 40 (FIG. 1) enables substantially higher applicator power operating levels for relatively deep tissue heating without excessive surface heating.

When the envelope outer surface 160 (FIG. 14) is in contact with the tissue region surface 162 coupling of the electric field radiated by the applicator 54 into the surrounding tissue region 32 is also enhanced. Assuming the cooling fluid 158 is distilled water or other fluid having a dielectric constant approximately equal to that of the surrounding tissue region 32 or a dielectric constant of approximately 50 at the mentioned operating frequency-the applicator external electric field lines 108 (FIG. 14), extend without substantial deflection or distortion through the cooling fluid into the tissue region. In effect, the cooling portion 44 enables the applicator apparatus 12 to conform to any irregularities, either normal or caused by malignant growths, of the body passage or cavity in which the apparatus is inserted for EMR heating purposes.

Although, depending upon radial cooling fluid thickness "R" (FIG. 14), at any particular point, that is, upon separation of the applicator 54 (FIG. 1) from the tissue region surface 162 (FIG. 14), some of the radiated electric field may not ordinarily extend through fluid, the amount of tissue heating electric field which extends into the tissue region 32 is none the less enhanced over that which would otherwise extend into the tissue were air voids present around the applicator 54. As a result, tissue heating characteristics are often improved even when tissue surface cooling is not required and localized hot spots, such as might otherwise be caused by energy reflections at air-tissue interfaces, are avoided. In this regard, when enhanced field coupling into the surrounding tissue region 32 is desired without tissue surface cooling, fluid flow through the envelope 138 is suitably restricted.

Although there have been described above specific arrangements of a body passage insertable applicator apparatus for use with electromagnetic radiation systems, and variations thereof in accordance with the invention, for purposes of illustrating the manner in which the invention may be used to advantage, it will be appreciated the invention is not limited thereto. Accordingly, any and all modifications, variations or equivalent arrangements which may occur to those skilled in the art should be considered to be within the scope of the invention as defined in the appendid claims.

What is claimed is:

1. A body insertable, electromagnetic radiation applicator apparatus for irradiating living tissue and the like comprising:
   (a) an electromagnetic energy transmission line for connection to a source of electromagnetic energy having a preselected frequency and transmitting electromagnetic energy; and
   (b) an applicator means operatively connected to the transmission line for receiving the electromagnetic energy, said applicator means including a segmented outer conductor, said segments thereof being spaced and having first and second ends, said segments decreasing in width from the first ends along the length of the applicator to the second ends for producing a substantially uniform field along substantially the entire length of the applicator when a transverse external electric heating field is radiated thereby, said applicator means responsive to the electromagnetic energy for producing substantially uniform heating electric fields whereby the tissue surrounding the applicator means is uniformly heated to a malignant cell damaging temperature thereby eliminating temperature regions where growth of malignant cells is stimulated.

2. A body insertable, electromagnetic radiation applicator apparatus for irradiating living tissue and the like comprising:
   (a) an electromagnetic energy transmission line having concentrically disposed inner and outer conductors for transmitting electromagnetic energy; and
   (b) an electromagnetic energy applicator means including inner and outer conductors having first and second ends, said inner and outer conductors having their first ends operatively connected to the corresponding inner and outer conductors of the electromagnetic energy transmission line, connector means for interconnecting the second ends of the inner and outer conductors, and a dielectric sheath means for enclosing the inner and outer conductors and connector means, said sheath means having portions above the outer conductor increasing in thickness from the first to the second ends of the outer conductor whereby the electric tissue heating field is longitudinally uniform.

3. A body insertable, electromagnetic radiation applicator apparatus according to claim 2, further including cooling means disposed around the applicator's sheath for cooling surrounding surfaces of body tissue and the like when the applicator is inserted in a body passage or cavity for irradiation.

4. A body insertable, electromagnetic radiation applicator apparatus according to claim 3, wherein the cooling means includes a flexible envelope for producing intimate envelope to body tissue contact, said flexible envelope disposed in fluid sealing relationship around the sheath and including cooling fluid inlet and outlet lines communicating from an outside to an inside of said bladder for enabling flow of cooling fluid there through.

5. A body insertable, electromagnetic radiation applicator apparatus according to claim 4, wherein said fluid inlet line has a fluid outlet end positioned relatively adjacent to said applicator emitting end and said fluid outlet line has a fluid receiving end relatively remote from said input line outlet end.

6. A body insertable, electromagnetic radiation applicator apparatus according to claim 4 wherein the cooling fluid comprises a dielectric media having a dielectric constant substantially equal to that of the living tissue and the like to be irradiated by the applicator apparatus, coupling of the electric field irradiated by the applicator into the living tissue and the like to be irradiated being thereby enhanced.

7. A body insertable electromagnetic radiation applicator apparatus according to claim 2 wherein the thickness of the dielectric sheath at the termination end of the applicator is equal to at least about one half of the diameter of the applicator.

8. A body insertable electromagnetic radiation applicator apparatus according to claim 2, wherein the applicator's outer conductor is segmented with adjacent pairs of edges of the outer conductor segments uniformly spaced apart.

9. A body insertable electromagnetic radiation applicator apparatus according to claim 2, wherein the outer conductor is helically split along the length of the applicator to enhance flexibility thereof.

10. A body insertable, electromagnetic radiation application apparatus according to claim 2, wherein said thickness of a transverse portion of the sheath covering the inner and outer conductor's second ends connector means is equal to at least about one half of the applicator's outer diameter.

11. A body insertable, electromagnetic radiation applicator according to claim 2 wherein the outer conductor is cylindrically shaped with a diameter decreasing from the first end to the second end consistent with the radial sheath thickness thereby maintaining a constant applicator apparatus diameter.

* * * * *